United States Patent [19]

Gamadia

[11] 3,995,778
[45] Dec. 7, 1976

[54] AEROSOL DISPENSING DEVICE

[75] Inventor: Rustom Kooverji Gamadia, London, England

[73] Assignee: Lever Brothers Company, New York, N.Y.

[22] Filed: Apr. 28, 1975

[21] Appl. No.: 572,483

Related U.S. Application Data

[63] Continuation of Ser. No. 428,991, Dec. 27, 1973, abandoned, which is a continuation of Ser. No. 243,138, April 12, 1972, abandoned.

[30] Foreign Application Priority Data

Apr. 23, 1971 United Kingdom .............. 11051/71

[52] U.S. Cl. ............................................. 222/399
[51] Int. Cl.² ....................................... B65D 83/14
[58] Field of Search ........................ 222/399, 386.5; 137/210

[56] References Cited

UNITED STATES PATENTS

| | | | |
|---|---|---|---|
| 1,607,579 | 11/1926 | Thompson, Jr. .................... | 222/399 |
| 2,772,922 | 12/1956 | Boyd et al. ......................... | 222/399 |
| 3,258,163 | 6/1966 | Brush ............................ | 222/399 X |
| 3,815,793 | 6/1974 | Morane et al. .................... | 222/399 |

Primary Examiner—Allen N. Knowles
Assistant Examiner—Norman L. Stack, Jr.
Attorney, Agent, or Firm—Arnold Grant

[57] ABSTRACT

This invention relates to an aerosol dispensing device for dispensing a substance free from liquified propellant. The device comprises a main compartment provided with a dispensing valve which contains the substance together with pressurized propellant vapor for effecting dispensation, and a reservoir compartment containing liquified propellant and pressurized propellant vapor. A communicating valve is provided between the reservoir compartment and the main compartment. The valve is adapted to open and allow propellant vapor to pass from the reservoir compartment to the main compartment. In a preferred arrangement the valve opens when dispensation to the atmosphere of the substance in the main compartment causes the pressure of the propellant vapor in that compartment to fall below the pressure of the propellant vapor in the reservoir by a predetermined amount.

2 Claims, 1 Drawing Figure

U.S. Patent     Dec. 7, 1976     3,995,778
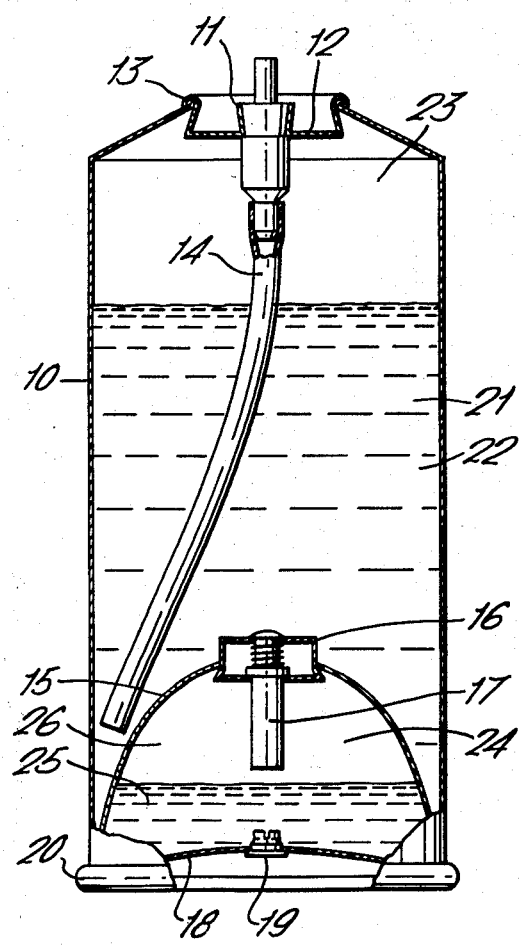

AEROSOL DISPENSING DEVICE

This is a continuation, of application Ser. No. 428,991, filed Dec. 27, 1973 now abandoned which is a continuation of Ser. No. 243,138, filed Apr. 12, 1972, also now abandoned.

This invention relates to an aerosol dispensing device. In a conventional aerosol dispensing device a substance to be dispensed is in admixture with a liquefied propellant and on actuation of the valve a mixture of the substance and the liquefied propellant is dispensed from the device. In some applications, dispensation of the substance together with liquefied propellant has disadvantages.

Numerous attempts at overcoming these disadvantages include the Continental Can Company's "Sepro" Can, and the "Sterigard" Dispenser, which are so-called "Bag-in-Can" systems, and venturi systems such as the "Preval Spraymaker" (Precision Valve Corporation) and "Innovair" (Geigy Chemical Corporation). Although these devices have been used on a small scale they are rather expensive to manufacture.

We have now developed a further device which maintains the substance to be dispensed free from liquefied propellant.

According to the present invention there is provided an aerosol dispensing device comprising a first compartment containing a substance to be dispensed and propellant solely in the vapour phase for dispensing the substance through the dispensing valve, a reservoir compartment containing liquefied propellant and propellant vapour and a communicating valve adapted to communicate the reservoir compartment with the first compartment and allow propellant vapour to pass from the reservoir compartment into the first compartment to augment the propellant in said compartment.

In a particular form the communicating valve is adapted to allow propellant vapour to pass from the reservoir compartment into the first compartment when dispensation of the substance in the first compartment to the atmosphere results in the propellant pressure in the first compartment falling below that of the propellant vapour in the reservoir compartment by a predetermined amount.

Normally the liquefied propellant will be one of the well-known hydrocarbon or halogenated hydrocarbon propellants.

The substance to be dispensed may be in any dispensible physical form although it is preferred that the substance is a powdered solid or a liquid or a dispersion of a powdered solid in a liquid.

For ease of manufacture the reservoir compartment is preferably formed within the body of the device between a dished dividing component and a base component.

Preferably the reservoir compartment is provided with inlet means for the introduction therein of the aerosol propellant and this may be in the form of a self-sealing gassing plug in the base component.

One example of an aerosol dispensing device according to the invention will be further described with reference to the single FIGURE of the accompanying drawing.

The device consists of a body component 10 having sloping shoulders and an open neck and base. A dispensing valve 11 set in a flange 12 is attached to the neck of the body component at the swaged joint 13. Dependent from the valve is a dip-tube 14 extending into the body component.

The open base of the body component 10 is closed by a dividing component 15 to form a first compartment 21 for containing a substance to be dispensed 22 together with pressurised propellant vapour 23 for dispensing the substance. The dividing component 15 is deeply dished into the body component 10 and together with a base component 18 attached to both the body and dividing members at the double swaged joint 20, forms a reservoir compartment 24 within the body component 10 and below the first compartment 21 for containing a liquefied aerosol propellant 25 together with pressurised propellant vapour 26. At the centre of the dished dividing component 15 a communicating valve 16, fitted with a septum tube 17 is provided, the valve being adapted to open and allow propellant vapour 26 to pass from the reservoir compartment 24 to the first compartment 21 when dispensation of the substance 22 to the atmosphere causes the pressure of the propellant vapour 23 in the first compartment 21 to fall below that of the vapour in the reservoir compartment by a predetermined amount.

The base component 13 is fitted with a channelised selfsealing plastic gassing plug 19 for the introduction of the liquefied propellant into the reservoir compartment 24.

The aerosol dispensing device according to the invention will normally be sold to the aerosol filler complete with the dividing component 15 and its valve 16 together with the base component 18 fitted with the self-sealing passing plug 19, although it is also envisaged that the individual components could be sold as a "kit-of-parts" for the filler to assemble during his filling procedure.

Some of the advantages of the specific embodiment described above with reference to the accompanying drawing are as follows. It is relatively simply and cheaply manufactured. The manufacture of the upper part of the device, that is the assembly of the body component 10, the dispensing valve 11 and the flange 12, is carried out in the same way as for a conventional aerosol dispensing device. As regards the lower part of the device, the dividing component 15 provided with the communicating valve 16 and the base component 18 may be attached to the body component 10 by a swaged joint. The two components may be swaged onto the body simultaneously or consecutively or they may be assembled together and the assemblage then swaged onto the body component 10.

As an alternative to utilising a pressure-sensitive communicating valve, this valve may be operated mechanically at the same time as the dispensing valve 11, for example by means of an operating rod connected to the valve stem of the dispensing valve. In this arrangement the communicating valve will preferably be fitted with a septum tube for leading propellant vapour into the headspace of the device.

The use of a reservoir compartment operating at a higher pressure than the pressure of the main compartment is advantageous in that the loss of pressure in the main compartment is quickly made good as soon as the communicating valve opens.

Another advantage is that since the reservoir is relatively small it requires only a small amount of propellant to maintain it at a relatively high pressure. Thus, together with the fact that no liquid propellant is wasted by dispensation to the atmosphere means that the device described above can be used to dispense substances at relatively high pressure without the necessity of using a large amount of propellant.

The adaption of a communicating valve fitted with a septum tube allows material to be dispensed from the device in any position whereas in some prior proposals for dispensing devices in which the substance to be dispensed is maintained free of liquid propellant, this is not possible.

In that the main compartment of the device is free of liquid propellant, the dispensing valve is less likely to clog and the possibility of corrosion is considerably reduced.

In a typical filling procedure for filling the embodiment of the device shown in the drawing, similar to that employed for filling the "Septo-Can," the substance to be dispensed is injected into the body component 10 of the device through the open neck, air is purged from the body and the pressure-release valve 11 is swaged into place. An aerosol propellant in liquefied form is then injected into the reservoir compartment through the plug 19. When the pressure in this compartment builds up to a predetermined level, the communicating valve 16 allows propellant vapour to pass into the upper compartment 21. The vapour pressure exerted in this compartment may be used to dispense the substance into the atmosphere through dispensing valve 11.

The device will be found useful for dispensing powders and such substances as feminine intimate hygiene products where co-dispensation of liquefied propellant produces undesirable product characteristics.

Another application of the device is in dispensing aqueous solutions which, in a conventional aerosol device, would form a separate phase above the liquefied propellant.

Two examples of formulations suitable for use in the device of the invention are as follows:

EXAMPLE 1

A hair setting lotion had the following composition:

|  | % by weight |
|---|---|
| National Starch Resyn 28-1310 (Trade Mark) | 2.00 |
| 2-amino-1,3-propanediol | 0.20 |
| Perfume | 0.10 |
| Industrial ethanol | 48.85 |
| Water | 48.85 |

The upper compartment of an aerosol dispensing device according to the invention was filled with about 100 gms of the above composition and about 10 gms of Freon 12 (Trade Mark) aerosol propellant was injected into the reservoir compartment. This amount of propellant is sufficient to dispense all of the lotion.

The high proportion of water in the composition produced a wet spray which effected a better set than a similar lotion based solely on alcohol. The lotion remained as a single homogeneous liquid phase in the upper compartment of the device, whereas if the setting lotion had been admixed with liquefied propellant in the normal way, two phases would have resulted, making it impossible to spray the lotion satisfactorily.

EXAMPLE 2

An aerosol talc had the following composition:

|  | % by weight |
|---|---|
| Tlac | 99.00 |
| Pyrogenic silica | 0.50 |
| Perfume | 0.50 |

The upper compartment of an aerosol dispensing device was filled with about 100 gms of the above composition and about 15 gms of Freon 12 (Trade Mark) aerosol propellant was injected into the reservoir compartment. This amount of propellant was sufficient to dispense all of the talc.

The talc was sprayed in a controllable jet having good directional characteristics. The chilling effect observed with talc aerosols formulated as suspensions of talc in a liquefied propellant was absent.

What is claimed is:

1. An aerosol dispensing device comprising a top outer wall, a bottom outer wall, a substantially cylindrical side outer wall, and an interior wall which divides the interior aerosol dispensing device into a first compartment and a second compartment wherein:
   a. the first compartment contains a substance to be dispensed and a liquefiable gas propellant in vapour phase;
   b. a dispensing valve extending through an outer wall interconnecting the first compartment and the atmosphere;
   c. the second compartment having an inlet through an exterior wall for introduction of a liquefied gas propellant, the second compartment containing liquefied gas propellant in liquid and vapour phase; the vapour pressure in the second compartment being higher than the vapour pressure in the first compartment; and,
   d. a communicating valve extending through the interior wall interconnecting the first and second compartments, the communicating valve permitting the passage of vapour phase propellant from the second to the first compartment while preventing passage of liquid phase propellant from the second to the first compartment; the communicating valve comprising an open ended tube extending from the interior wall part way into the first compartment and part way into the second compartment, the amount of liquid propellant in the second compartment and the extension of the communicating valve from the interior wall into the second compartment being such that the open end of the communicating valve in the second compartment is always above the levels of the liquefied gas propellant whatever the position of the device; and the communicating device having a resillient member which completely circumnavigates the communicating valve in the first compartment and holds the communicating valve closed except when the gas pressure difference between the first and the second compartments rises to a predetermined level following dispensation of the substance from the first compartment.

2. An aerosol dispensing device having a top outer wall, a bottom outer wall, a substantially cylindrical side outer wall and an interior wall, consisting essentially of:
   a. the first compartment being adapted to contain a substance to be dispensed and a liquefiable gas propellant in vapour phase;

b. a dispensing valve extending through an outer wall interconnecting the first compartment and the atmosphere;
c. a second compartment within the device having as one of its boundaries the interior wall, and having an inlet through an exterior wall for introduction of a liquefied gas propellant, said second compartment being adapted to contain a liquefied gas propellant in liquid and vapour form; and,
d. a communicating valve extending through the interior wall interconnecting the first and second compartments, the communicating valve permitting the passage of vapour phase propellant from the second to the first compartment while preventing passage of liquid phase propellant from the second to the first compartment; the communicating valve comprising an open ended tube extending from the interior wall part way into the first compartment and part way into the second compartment, the amount of liquid propellant in the second compartment and the extension of the communicating valve from the interior wall into the second compartment being such that the open end of the communicating valve in the second compartment is always above the levels of the liquefied gas propellant whatever the position of the device; and the communicating device having a resillient member which completely circumnavigates the communicating valve in the first compartment and holds the communicating valve closed except when the gas pressure difference between the first and the second compartments rises to a predetermined level following dispensation of the substance from the first compartment.

* * * * *